| United States Patent [19] | [11] | 4,424,143 |
|---|---|---|
| Shiozaki et al. | [45] | Jan. 3, 1984 |

[54] CATALYST FOR OXYCHLORINATION OF ETHYLENE

[75] Inventors: Ken Shiozaki, Hyogo; Akira Ohnishi, Kakogawa, both of Japan

[73] Assignee: Kanegafuchi Kagaku Kogyo Kabushiki Kaisha, Osaka, Japan

[21] Appl. No.: 364,028

[22] Filed: Mar. 31, 1982

[30] Foreign Application Priority Data

Apr. 6, 1981 [JP] Japan .................................. 56-51971

[51] Int. Cl.$^3$ ............................................. B01J 27/10
[52] U.S. Cl. .................................... 502/225; 570/243; 570/245
[58] Field of Search ................. 252/441; 570/243, 245

[56] References Cited

U.S. PATENT DOCUMENTS

| 3,867,469 | 2/1975 | Ricks | 252/441 X |
| 3,892,816 | 7/1975 | Kister | 260/659 A |
| 4,124,534 | 11/1978 | Leitert et al. | 252/441 |

Primary Examiner—Patrick Garvin
Attorney, Agent, or Firm—Armstrong, Nikaido, Marmelstein & Kubovcik

[57] ABSTRACT

A catalyst suitable for use in the preparation of 1,2-dichloroethane by oxychlorination of ethylene containing cupric chloride and, as a promotor, a combination of potassium chloride and cesium chloride, which can inhibit production of ethyl chloride by-product and has excellent selectivity to 1,2-dichloroethane and catalyst life.

3 Claims, No Drawings

CATALYST FOR OXYCHLORINATION OF ETHYLENE

BACKGROUND OF THE INVENTION

The present invention relates to a catalyst suitable for use in production of 1,2-dichloroethane using a mixed gas of ethylene, hydrogen chloride and air or oxygen, and more particularly to a supported cupric chloride-potassium chloride-cesium chloride catalyst suitable for use in oxychlorination of ethylene which can inhibit the by-production of ethyl chloride so as to produce 1,2-dichloroethane in high yields.

In fixed-bed oxychlorination systems, a cupric chloride catalyst is generally employed. The addition reaction of ethylene and hydrogen chloride to produce ethyl chloride and the combustion reaction of ethylene occupy a large proportion of the side reactions in the selective oxychlorination of ethylene. It is known that the use of potassium chloride as a promotor is particularly effective for inhibiting the by-production of ethyl chloride. However, in order to obtain a sufficient effect of the addition of potassium chloride promotor to cupric chloride on the inhibition of the ethyl chloride by-production, the potassium chloride/cupric chloride mixing ratio must be raised up to about 0.5/1 by weight, and on the other hand, whereby the activity of the catalyst is remarkably lowered with increasing the mixing ratio of potassium chloride.

Many selective oxychlorination catalysts for the conversion of ethylene to 1,2-dichloroethane have been proposed. According to the present inventors' study on these catalysts using an activated alumina carrier, however, no catalysts superior in reaction characteristics to cupric chloride-potassium chloride catalysts have been found.

SUMMARY OF THE INVENTION

It has now been found that a novel catalyst capable of inhibiting the by-production of ethyl chloride can be obtained by employing a combination of potassium chloride and cesium chloride as a promotor for cupric chloride catalyst.

In accordance with the present invention, there is provided a catalyst for use in preparation of 1,2-dichloroethane by oxychlorination of ethylene which contains cupric chloride as a main component and a combination of potassium chloride and cesium chloride as a promotor.

DETAILED DESCRIPTION

The catalyst of the present invention is particularly useful for the preparation of 1,2-dichloroethane in fixed-bed oxychlorination systems.

When potassium chloride and cesium chloride are employed in combination as a promotor for the cupric chloride catalyst, the inhibitory effect on the ethyl chloride by-production which can not be obtained by the use of, as a promotor, an alkali metal alone such as potassium chloride, sodium chloride or cesium chloride, an alkaline earth metal alone or a combination of the alkali metal and the alkaline earth metal, can be remarkably increased, and moreover, the influence on the lowering of the catalyst activity is less than the case using potassium or cesium chloride alone as a promotor. It is known that an alkali metal or an alkaline earth metal is incorporated in cupric chloride in order to inhibit the vaporization of copper and to increase the selectivity to 1,2-dichloroethane. However, it has not been known that the by-production of ethyl chloride can be greatly decreased without lowering the catalyst activity by the catalyst composition containing of cupric chloride, potassium chloride and cesium chloride.

The catalyst composition is supported on a carrier having a suitable specific surface area, e.g. activated alumina or silica gel. In practice, activated alumina having both micro-pores and macro-pores is suitable as a carrier for the catalyst composition of the present invention. Particularly suitable in effectively exhibiting the catalyst activity are activated alumina carriers having a specific surface area of 100 to 350 $m^2./g.$ and having a volume of the pores having a semidiameter of at least 100 angstroms in the range of at least 20% to the total volume of the whole pores. The total content of cupric chloride, potassium chloride and cesium chloride in the carrier-supported catalyst of the present invention is from 5 to 25% by weight to the total weight of the catalyst composition and the carrier. It is preferable that the catalyst composition contains cupric chloride, potassium chloride and cesium chloride in a ratio of 1:0.05 to 0.7:0.05 to 0.7 by weight, especially 1:0.1 to 0.5:0.1 to 0.5 by weight. Also, it is particularly preferable that the ratio of cesium chloride to potassium chloride is within the range of 0.5 to 2.0:1 by weight.

In case of supporting the catalyst composition of the present invention on a carrier, the respective components may be not in their active forms, i.e. chlorides of copper, potassium and cesium, and there may also be employed copper, potassium and cesium sources which are soluble in water and are convertible to cupric chloride, potassium chloride and cesium chloride in reaction systems, e.g. cuprous chloride, cupric nitrate and cesium carbonate. In general, the catalytic agents are supported on a carrier in the form of the chlorides. For instance, an activated alumina carrier is immersed in an aqueous solution of cupric chloride, potassium chloride and cesium chloride so as to be impregnated with the solution, and the excess solution is then separated by filtration and the impregnated carrier is dried to give a supported catalyst.

The present invention is more specifically described and explained by means of the following Examples and Comparative Examples, in which all % are by weight unless otherwise noted. It is to be understood that the present invention is not limited to the Examples and various changes and modifications may be made in the invention without departing from the spirit and scope thereof.

In the following Examples and Comparative Examples, oxychlorination of ethylene was carried out by employing a vertical reactor composed of a nickel tube of 26.3 mm. in inner diameter and 1,200 mm. in length, a steel jacket of 2 inches (about 51 mm.) in inner diameter which was provided round the nickel tube and in which a liquid heat medium (registered trademark "Dowtherm" made by Dow Chemical Co.) was circulated, and a nickel pipe for temperature measurement of 7 mm. in outer diameter inserted into the central portion of the above nickel tube.

A catalyst was mixed with columnar graphite particles having a height of 5 mm. and a diameter of 5 mm. to dilute in a concentration of 50% by volume, and 205 ml. of the thus diluted catalyst was packed in the upper half of the reactor. Also, 205 ml. of the nondiluted catalyst was packed in the lower half of the reactor. The reaction was carried out by introducing a reactant gas from the top of the reactor and taking out the reaction gas from the bottom of the reactor. As a reactant gas, 40 Nl/hour of hydrogen chloride, 21.6 Nl/hour of ethylene and 57 Nl/hour of air were supplied to the reactor, and the pressure at the outlet of the reactor was kept at atmospheric pressure. The reaction temperature was controlled by adjusting the temperature of the heat medium in the jacket so that the conversion of the hydrogen chloride fed was maintained 99%. The reaction gas taken out was cooled in two stages first to 5° C. and then to −35° C., and the condensed reaction product and the uncondensed reaction gas were analyzed by gas chromatography in a usual manner.

EXAMPLES 1 TO 12 AND COMPARATIVE EXAMPLES 1 TO 9

Catalysts were prepared by a usual immersion method by employing a commercially available alumina molding having the following characteristics as a carrier.

[Characteristics of activated alumina used]
Particle size: 4 to 5 meshes (spherical)
Specific surface area: 197 m²./g.
Total pore volume: 0.58 ml./g.

Eight kinds of catalysts were prepared, i.e. $CuCl_2$-KCl system, $CuCl_2$-CsCl system, $CuCl_2$-NaCl system, $CuCl_2$-LiCl system, $CuCl_2$-MaCl$_2$ system, $CuCl_2$-KCl-CsCl system, $CuCl_2$-KCl-NaCl system and $CuCl_2$-NaCl-CsCl system. For instance, the $CuCl_2$-KCl-CsCl catalyst of Example 1 was prepared by dissolving 66.4 g. of cupric chloride dihydrate, 18.7 g. of potassium chloride and 18.7 g. of cesium chloride in distilled water, adjusting the volume of the aqueous solution to 338 ml., soaking 500 g. of the above activated alumina particles in the aqueous solution at a temperature of 20° to 40° C. for 1 hour, draining off the excess solution and drying the impregnated catalyst particles at 150° C. for 2 hours and, finally, at 250° C. for 2 hours. The thus prepared supported catalyst contained 10.9% of $CuCl_2$, 3.1% of KCl and 3.0% of CsCl. The catalysts having the compositions shown in Table 1 and 2 were also prepared according to the above procedure.

The oxychlorination of ethylene was carried out by employing the thus prepared catalysts.

The results are shown in Tables 1 and 2.

Also, the oxychlorination test of Example 2 was continued for 1,000 hours. During that time, no changes in conversion of hydrogen chloride, temperature distribution and composition of by-products were observed.

TABLE 1

| | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|
| Composition of supported catalyst (%) | | | | | | | | | | | | |
| $CuCl_2$ | 10.9 | 12.5 | 16.2 | 10.0 | 11.3 | 11.5 | 11.0 | 11.1 | 13.9 | 10.0 | 11.0 | 10.8 |
| KCl | 3.1 | 2.5 | 2.0 | 3.5 | 4.6 | 2.5 | 4.8 | 1.6 | 1.0 | 6.0 | 6.0 | 0.8 |
| CsCl | 3.0 | 2.5 | 2.0 | 4.0 | 2.5 | 3.8 | 1.6 | 4.7 | 1.0 | 5.3 | 0.8 | 5.1 |
| Weight ratio of promotor to $CuCl_2$ | | | | | | | | | | | | |
| KCl/$CuCl_2$ | 0.28/1 | 0.20/1 | 0.12/1 | 0.35/1 | 0.41/1 | 0.22/1 | 0.44/1 | 0.14/1 | 0.07/1 | 0.60/1 | 0.55/1 | 0.07/1 |
| CsCl/$CuCl_2$ | 0.28/1 | 0.20/1 | 0.12/1 | 0.40/1 | 0.22/1 | 0.33/1 | 0.15/1 | 0.42/1 | 0.07/1 | 0.53/1 | 0.07/1 | 0.47/1 |
| Heat medium temperature (°C.) | 204 | 200 | 197 | 209 | 208 | 206 | 207 | 205 | 192 | 225 | 208 | 205 |
| Hot spot temperature (°C.) | 286 | 288 | 291 | 290 | 289 | 290 | 288 | 291 | 291 | 300 | 292 | 290 |
| Conversion of HCl (%) | 98.9 | 99.0 | 99.2 | 98.8 | 98.9 | 99.0 | 99.0 | 99.1 | 99.3 | 98.8 | 99.0 | 99.1 |
| Selectivity (%) | | | | | | | | | | | | |
| 1,2-Dichloroethane | 98.2 | 97.9 | 97.6 | 98.1 | 97.8 | 97.9 | 97.6 | 97.4 | 96.3 | 95.9 | 96.5 | 96.8 |
| Ethyl chloride | 0.21 | 0.23 | 0.32 | 0.23 | 0.24 | 0.24 | 0.28 | 0.30 | 0.60 | 0.52 | 0.48 | 0.46 |
| Other chlorides | 0.7 | 0.8 | 1.0 | 0.7 | 0.8 | 0.9 | 1.1 | 1.2 | 1.8 | 1.5 | 1.6 | 1.4 |
| Combustion rate of ethylene (%) | 0.9 | 1.1 | 1.1 | 1.0 | 1.2 | 1.0 | 1.0 | 1.1 | 1.3 | 2.1 | 1.4 | 1.3 |

TABLE 2

| | Com. Ex. 1 | Com. Ex. 2 | Com. Ex. 3 | Com. Ex. 4 | Com. Ex. 5 | Com. Ex. 6 | Com. Ex. 7 | Com. Ex. 8 | Com. Ex. 9 |
|---|---|---|---|---|---|---|---|---|---|
| Composition of supported catalyst (%) | | | | | | | | | |
| $CuCl_2$ | 10.9 | 12.5 | 11.8 | 14.2 | 11.1 | 12.6 | 12.5 | 11.2 | 11.0 |
| KCl | 6.0 | 5.0 | — | — | — | — | — | 3.0 | — |
| CsCl | — | — | 5.2 | 4.1 | — | — | — | — | 3.0 |
| NaCl | — | — | — | — | 4.9 | — | — | 2.9 | 3.0 |
| LiCl | — | — | — | — | — | 3.5 | — | — | — |
| $MgCl_2$ | — | — | — | — | — | — | 4.0 | — | — |
| Weight ratio of promotor to $CuCl_2$ | | | | | | | | | |
| KCl/$CuCl_2$ | 0.55/1 | 0.40/1 | — | — | — | — | — | 0.27/1 | — |
| CsCl/$CuCl_2$ | — | — | 0.44/1 | 0.29/1 | — | — | — | — | 0.27/1 |
| NaCl/$CuCl_2$ | — | — | — | — | 0.44/1 | — | — | 0.26/1 | 0.27/1 |
| LiCl/$CuCl_2$ | — | — | — | — | — | 0.28/1 | — | — | — |
| $MgCl_2$/$CuCl_2$ | — | — | — | — | — | — | 0.32/1 | — | — |
| Heat medium temperature (°C.) | 211 | 206 | 205 | 198 | 195 | 221 | 218 | 203 | 202 |
| Hot spot temperature (°C.) | 293 | 288 | 292 | 290 | 287 | 296 | 294 | 287 | 288 |
| Conversion of HCl (%) | 98.9 | 99.0 | 99.1 | 99.0 | 99.2 | 98.7 | 98.9 | 98.9 | 99.2 |
| Selectivity (%) | | | | | | | | | |
| 1,2-Dichloroethane | 96.4 | 96.6 | 96.5 | 96.2 | 95.0 | 93.3 | 91.9 | 96.4 | 96.5 |
| Ethyl chloride | 0.56 | 0.53 | 0.51 | 0.57 | 1.2 | 2.3 | 3.8 | 0.84 | 0.77 |
| Other chlorides | 1.6 | 1.6 | 1.5 | 1.7 | 2.0 | 2.4 | 2.7 | 1.6 | 1.5 |
| Combustion rate of ethylene (%) | 1.4 | 1.3 | 1.5 | 1.5 | 1.8 | 2.0 | 1.6 | 1.2 | 1.2 |

From the above Examples, it is clear that the CuCl$_2$-KCl-CsCl catalyst of the present invention shows production of a decreased amount of ethyl chloride by-product as compared with the other catalyst systems, and has an excellent selectivity to 1,2-dichloroethane and an excellent catalyst life.

In addition to the ingredients used in the Examples, other ingredients can be used in the Examples as set forth in the specification to obtain substantially the same results.

What we claim is:

1. A catalyst for use in the preparation of 1,2-dichloroethane from ethylene in a fixed-bed oxychlorination system which contains cupric chloride, potassium chloride and cesium chloride in a CuCl$_2$/KCl/CsCl ratio of 1:0.1 to 0.5:0.1 to 0.5 by weight.

2. The catalyst of claim 1, wherein the cupric chloride, potassium chloride and cesium chloride are supported on an activated alumina having a specific surface area of from 100 to 350 m$^2$/g.

3. A fixed-bed oxychlorination system catalyst for preparing 1,2-dichloroethane from ethylene which consists of an activated alumina support having a surface area of 100 to 350 m$^2$/g with a catalyst thereon, the catalyst comprising cupric chloride, potassium chloride and cesium chloride in a CuCl$_2$/KCl/CsCl ratio of 1:0.1 to 0.5:0.1 to 0.5 by weight.

* * * * *